(12) United States Patent
Gatto et al.

(10) Patent No.: US 8,907,154 B2
(45) Date of Patent: Dec. 9, 2014

(54) SANITARY NAPKINS WITH HYDROPHOBIC LOTIONS

(71) Applicant: The Proctor & Gamble Company, Cincinnati, OH (US)

(72) Inventors: Joseph Anthony Gatto, Loveland, OH (US); Raphael Warren, Cincinnati, OH (US); John Lee Hammons, Fairfield Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/790,563

(22) Filed: Mar. 8, 2013

(65) Prior Publication Data

US 2014/0257216 A1   Sep. 11, 2014

Related U.S. Application Data

(63) Continuation of application No. 11/222,654, filed on Sep. 9, 2005, now abandoned, which is a continuation-in-part of application No. 10/152,924, filed on May 21, 2002, now abandoned, which is a continuation of application No. 09/968,154, filed on Oct. 1, 2001, now abandoned.

(51) Int. Cl.
*A61F 13/15*   (2006.01)

(52) U.S. Cl.
USPC ............................. 604/359; 604/367; 604/360

(58) Field of Classification Search
USPC .......................................... 604/359, 360, 367
See application file for complete search history.

(56) References Cited

U.S. PATENT DOCUMENTS

| | | | |
|---|---|---|---|
| 3,489,148 A | 1/1970 | Duncan et al. |
| 3,896,807 A | 7/1975 | Buchalter |
| 4,911,932 A | 3/1990 | Clum et al. |
| 5,445,823 A | 8/1995 | Hall et al. |
| 5,607,760 A | 3/1997 | Roe |
| 5,609,587 A | 3/1997 | Roe |
| 5,635,191 A | 6/1997 | Roe et al. |

(Continued)

FOREIGN PATENT DOCUMENTS

| | | |
|---|---|---|
| DE | 108036 A2 | 9/1974 |
| DE | 3444464 A1 | 1/1986 |

(Continued)

OTHER PUBLICATIONS

PCT International Search Report dated Dec. 27, 2007.

*Primary Examiner* — Jacqueline F. Stephens
(74) *Attorney, Agent, or Firm* — Andres E. Velarde (57) ABSTRACT

A catamenial device comprising a liquid pervious topsheet, the topsheet having an inner surface oriented toward the interior of the absorbent article and an outer surface oriented toward the body of the wearer when the absorbent article is being worn. At least a portion of the topsheet outer surface comprises an effective amount of a lotion coating which is semi-solid or solid at about 25° C. and which is partially transferable to the wearer's body. The lotion coating comprises from about 60 to about 99.9% of a carrier comprising a petroleum based hydrocarbon and lower molecular weight glycols or polyols and from about 0.2 to about 65% of a fatty alcohol with a melting point from about 450 C to about 110° C. A backsheet is joined to the topsheet and an absorbent core is disposed between the topsheet and the backsheet.

19 Claims, 1 Drawing Sheet

(56) References Cited

U.S. PATENT DOCUMENTS

| | | |
|---|---|---|
| 5,643,588 A | 7/1997 | Roe et al. |
| 5,968,025 A | 10/1999 | Roe et al. |
| 5,998,032 A | 12/1999 | Hansen et al. |
| 6,107,537 A | 8/2000 | Elder et al. |
| 6,118,041 A | 9/2000 | Roe et al. |
| 6,149,924 A | 11/2000 | Paul |
| 6,217,890 B1 | 4/2001 | Paul et al. |
| 6,340,411 B1 | 1/2002 | Hansen et al. |
| 6,426,444 B2 | 7/2002 | Roe et al. |
| 6,475,197 B1 | 11/2002 | Krzysik et al. |
| 6,497,893 B1 | 12/2002 | Everhart et al. |
| 6,503,524 B1 | 1/2003 | Tyrrell et al. |
| 6,515,029 B1 | 2/2003 | Krzysik et al. |
| 6,541,692 B2 | 4/2003 | Miller |
| 6,586,652 B1 | 7/2003 | Roe et al. |
| 6,706,946 B1 | 3/2004 | Lankhof et al. |
| 6,720,006 B2 | 4/2004 | Hanke et al. |
| 6,756,520 B1 | 6/2004 | Krzysik et al. |
| 6,825,393 B2 | 11/2004 | Roe et al. |
| 6,861,571 B1 | 3/2005 | Roe et al. |
| 6,888,044 B2 | 5/2005 | Fell et al. |
| 7,166,292 B2 | 1/2007 | Isele et al. |
| 2001/0009991 A1 | 7/2001 | Hisanaka |
| 2002/0120241 A1 | 8/2002 | Tyrrell et al. |
| 2002/0120242 A1 | 8/2002 | Tyrrell et al. |
| 2003/0082219 A1 | 5/2003 | Warren et al. |
| 2003/0206943 A1 | 11/2003 | Hammons et al. |
| 2003/0206979 A1 | 11/2003 | Dvoracek et al. |
| 2004/0167479 A1 | 8/2004 | Warren et al. |
| 2004/0170589 A1 | 9/2004 | Gatto |
| 2005/0010183 A1 | 1/2005 | Miller et al. |
| 2005/0112078 A1 | 5/2005 | Boddupalli et al. |
| 2005/0129651 A1 | 6/2005 | Gatto et al. |
| 2005/0148962 A1 | 7/2005 | Warren et al. |
| 2005/0154362 A1 | 7/2005 | Warren et al. |
| 2006/0062816 A1 | 3/2006 | Gatto et al. |
| 2006/0140899 A1 | 6/2006 | Koenig et al. |
| 2006/0184150 A1 | 8/2006 | Noel |
| 2007/0219515 A1* | 9/2007 | Marsh et al. .................. 604/359 |
| 2007/0286876 A1 | 12/2007 | Warren et al. |

FOREIGN PATENT DOCUMENTS

| | | |
|---|---|---|
| DE | 4136540 A1 | 5/1992 |
| DE | 4401308 A1 | 7/1995 |
| EP | 95615 A2 | 12/1983 |
| EP | 769291 A2 | 4/1997 |
| EP | 1051958 A1 | 11/2000 |
| EP | 1120097 A2 | 8/2001 |
| WO | 9717060 A1 | 5/1997 |
| WO | 9918919 A2 | 4/1999 |
| WO | 9945973 A1 | 9/1999 |
| WO | 9945974 A1 | 9/1999 |
| WO | 9953907 A2 | 10/1999 |
| WO | 9955303 A1 | 11/1999 |
| WO | WO0117501 A2 | 3/2001 |
| WO | WO0117564 A2 | 3/2001 |
| WO | WO0117565 A2 | 3/2001 |
| WO | WO0118181 A2 | 3/2001 |
| WO | 02/087517 | 11/2002 |
| WO | WO02087517 A2 | 11/2002 |
| WO | WO03028776 A2 | 4/2003 |

* cited by examiner

SANITARY NAPKINS WITH HYDROPHOBIC LOTIONS

CROSS REFERENCE TO RELATED APPLICATION

This application is a continuation of U.S. Ser. No. 11/222,654, filed Sep. 9, 2005, pending, which is a continuation-in-part of U.S. Ser. No. 10/152,924, filed on May 21, 2002, abandoned, which is a continuation-in-part of U.S. Ser. No. 09/968,154, filed Dec. 1, 2001, abandoned. All incorporated herein by reference.

FIELD OF INVENTION

This application relates to catamenial devices such as sanitary napkins for the absorption of menses. More particularly, the present invention relates to catamenial devices having a hydrophobic lotion coating on the outer surface of the topsheet, the lotion being transferable to the wearers skin by normal contact and wearer motion and/or body heat.

BACKGROUND OF THE INVENTION

Disposable absorbent articles, such as diapers, training pants, and catamenial devices having lotioned topsheets are known. Lotions of various types are known to provide various skin benefits, such as prevention or treatment of diaper rash. These lotions can be applied to the topsheet of absorbent articles, for example, and can be transferred to the body of the wearer during use.

Unlike many types of disposable absorbent articles, catamenial devices, such as pads and pantyliners are specifically designed to acquire menstrual fluid. Menstrual fluid differs from other exudates, such as urine, in many important properties, such as viscosity and chemical composition. Therefore, catamenial devices should differ in their structural components from such devices as baby diapers to be optimized for the maximum absorption of menstrual fluid.

The addition of lotion to the topsheet of absorbent articles is known to provide benefits such as easier BM clean up on babies. Likewise, lotion on topsheets is known to provide for better skin health of babies, such as the reduction of diaper rash. For example, U.S. Pat. No. 3,489,148 to Duncan et al. teaches a baby diaper comprising a hydrophobic and oleophobic topsheet wherein a portion of the topsheet is coated with a discontinuous film of oleaginous material. A major disadvantage of the diapers disclosed in the Duncan et al. reference is that the hydrophobic and oleophobic topsheets are slow in promoting transfer of urine to the underlying absorbent cores. Since the viscosity of menses is considerably greater than urine, the problems associated with Duncan et al are more profound.

One successful attempt at overcoming the problems of Duncan is disclosed in Roe et al., U.S. Pat. No. 5,968,025. Roe et al. discloses an absorbent article in which a lotion is applied to a hydrophilic topsheet (or a topsheet rendered to be hydrophilic). The hydrophilic topsheet aids in ensuring urine gushes are adequately absorbed into the underlying core, rather than running off into the sides of a baby diaper, for example.

The known attempts at applying lotions to topsheets of absorbent products have been primarily directed to baby diapers, with the benefit provided being better skin health for the bottom of the baby. Little attention has been directed to the unique problems associated with the body of an adult woman when wearing a catamenial pad. The vulvar area of an adult woman is very different than that of a baby's bottom (or buttock skin in general). The vulvar region is understood to include the region from the posterior gluteal groove and perineum to the anterior mons pubis and laterally between the intertriginous zones. Given very different skin surfaces, and the lotion needs are very different. For example, rather than being concerned with diaper rash, a menstruating woman is more concerned about personal hygiene, that is, reducing the amount of menses remaining on the skin or hair ('body') after use of a sanitary pad.

The aforementioned attempts at providing a lotion on a topsheet of an absorbent article have focused on the lotion/topsheet characteristics necessary to handle a gush of urine in a relatively short amount of time. However, for catamenial devices, the fluid insult has very different characteristics, in the context of physio-chemical properties (e.g., viscosity, fluid dynamics, etc.) and in the volume and in the time to be absorbed. For example, menstrual flow typically consists of two patterns. One of these is "trickle" flow, which varies from 0.1 to 2 ml per hour. The second pattern is "gush" flow which varies from a few ml in volume delivered over a few seconds. Gush flow can result from an accumulation of menses pooling in the vagina which can then exit the body upon a change in position, such as a transition from sitting to standing. In any event, even with gush flow, the total amount of fluid required to be absorbed into the core in a given time is much less than that required by other absorbent products, such as baby diapers, for example. One practical result is that catamenial devices, rather than needing to be designed to handle gushing fluid, more typically handle fluid through a "blotting" effect.

Accordingly, there is a need for an improvement in catamenial devices to improve the skin hygiene of menstruating women.

Additionally, there is a need for a catamenial device having improved fluid handling such that more menses enter into and remain in the device, and less on the skin or hair of the wearer.

SUMMARY OF THE INVENTION

A catamenial device comprising a liquid pervious topsheet, the topsheet having an inner surface oriented toward the interior of the absorbent article and an outer surface oriented toward the body of the wearer when the absorbent article is being worn. At least a portion of the topsheet outer surface comprises an effective amount of a lotion coating which is semi-solid or solid at about 25° C. and which is partially transferable to the wearer's body. The lotion coating comprises from about 60 to about 99.9% of a carrier comprising a petroleum based hydrocarbon and lower molecular weight glycols or polyols and from about 0.2 to about 65% of a fatty alcohol with a melting point from about 450 C to about 110° C. A backsheet is joined to the topsheet and an absorbent core is disposed between the topsheet and the backsheet.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

DETAILED DESCRIPTION OF THE INVENTION

Figure 1:
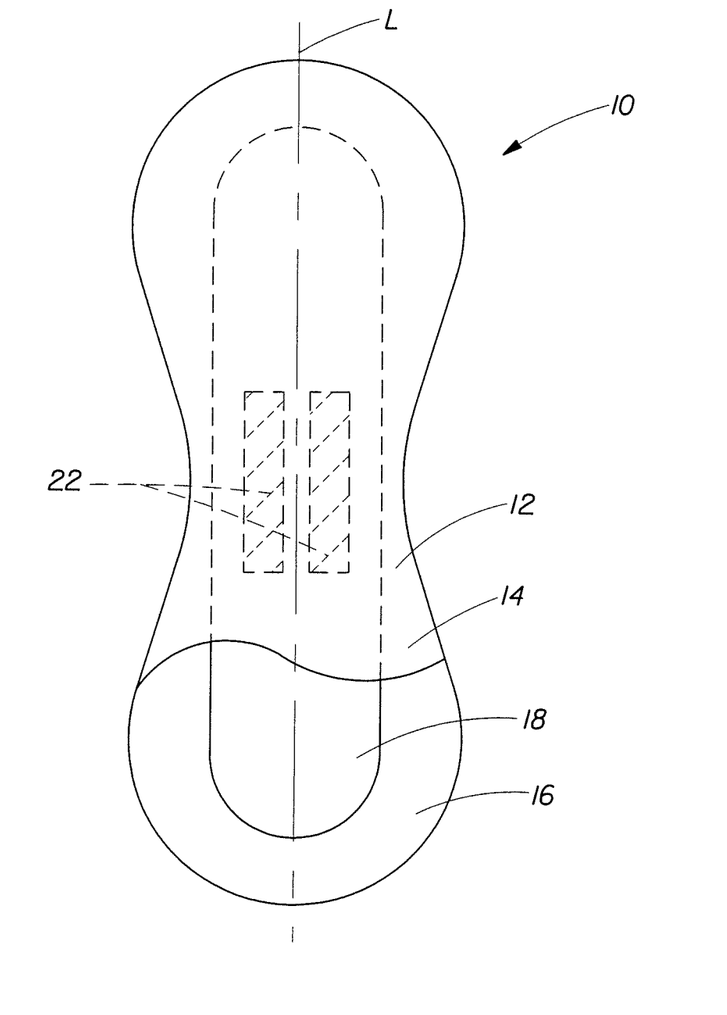
FIG. 1 is a perspective view of a catamenial device having a topsheet and a lotion composition.

FIG. 1 shows a catamenial device 10, that can be a sanitary napkin or pantiliner, having a body-contacting surface 12 comprising a topsheet 14, a liquid impervious backsheet 16 joined to the topsheet 14, an absorbent core 18. The sanitary napkin 10 has a longitudinal axis L and may also be provided with additional features commonly found in napkins, including "wings" or "flaps" (not shown) as is known in the art, and, and/or a fluid acquisition layer to promote fluid transport to the absorbent core 18. Likewise, the topsheet of the sanitary napkin can have various optional characteristics, as is known in the art. For example, the topsheet 14 can have channels embossed therein to direct fluid flow, and can have apertures there through to aid in fluid acquisition. The topsheet 14 of the catamenial device 10 of the present invention has a lotion composition 22 disposed onto the topsheet.

The topsheet 14 and lotion composition 22 of the present invention offer significant advantages over known topsheets and lotions. In particular, in a preferred embodiment, the topsheet 14 is hydrophobic or rendered to be hydrophobic, and the lotion is also hydrophobic. The levels of hydrohobicity can be determined by standard techniques, such as measuring angles that a drop of water make on a surface of material at equilibrium. In general, for the purposes of this invention, a material is considered hydrophobic if a drop of water exhibits an angle of about 60 degrees or greater. Fibers are considered to be hydrophobic if film sheets formed from the polymers of the fibers would exhibit contact angles with water greater than 60 degrees, more preferably 75 degrees, and even more preferably greater than about 90 degrees. Contact angles as a measure of hydrophobicity are well known in the art, and methods for measuring contact angles are equally well known. As is well known, contact angles greater than about 90 degrees are considered hydrophobic, and contact angles less than 90 degrees are considered hydrophilic. As used herein, however, contact angles of 60 degrees or greater are considered hydrophobic. The levels of hydrophobicity of the topsheet and lotion, respectively, can be equal, or the hydrophobicity of the lotion can be greater than the hydrophobicity of the topsheet. In use, the lotion can transfer from the topsheet to the skin of the wearer, which serves to make the skin and hair hydrophobic as well.

The advantage of the present invention can be appreciated with an understanding of the difference between menstrual fluid flow and urine flow in babies, for example. Topsheets of baby diapers are generally taught to be hydrophilic, with or without a lotion applied, such that sudden gushes of urine can be acquired through the topsheet and into the core with minimal runoff of fluid. However, it has been discovered that menstrual fluid, which has a much greater viscosity and much lower fluid flow, both in quantity and time, can be very effectively handled with a hydrophobic topsheet. Whereas urine may simply run off of a hydrophobic topsheet, particularly one that is treated with a hydrophobic lotion, it has unexpectedly been found that such a structure provides for superior benefits in a catamenial pad for menstruating women. Another unexpected benefit is the coating of the skin and hair of the vulvar region during use of a catamenial device of the present invention that results in cleaner skin and hair of the vulvar region. Yet, another benefit is better fluid acquisition of the fluid due to transfer of the lotion to the skin of the wearer that minimizes fluid transport on the skin and hair of the wearer away from the point of exit.

Without being bound by theory, it is believed that the superior benefits of the present invention are best exhibited by the combination of a hydrophobic topsheet and a hydrophobic lotion. A lotion is considered hydrophobic, for example, if the hydrophilic/lipophilic balance (HLB) is less than or equal to 7.

The lotion compositions of the present invention can comprise a select combination of body treatment agents such as hexamidine, zinc oxide, and niacinamide which are highly effective in the prevention and treatment of erythema, malodor, and bacterial skin disorders, especially when these lotion compositions are administered to the body from application on absorbent articles.

The term "body treatment agent" as used herein to include treatments effective on skin or hair of mammalian bodies, and refers to materials that when transferred to the body are capable of preventing, reducing, and/or eliminating occurrences of skin disorders, particularly skin disorders associated with erythema, malodor, and bacterial infections. The term "skin disorders" as used herein refers to symptoms associated with irritating, acute, or chronic skin abnormalities. Examples of such symptoms include, but are not limited to, itching, inflammation, rash, burning, stinging, redness, swelling, sensitivity, sensation of heat, flaking/scaling, malodor, and the like. The term "ambient conditions" as used herein refers to surrounding conditions at about one atmosphere of pressure, at about 50% relative humidity, and at about 25° C.

The lotion compositions of the present invention can comprise, consist of, or consist essentially of the elements and limitations of the invention described herein, as well as any of the additional or optional ingredients, components, or limitations described herein. All percentages, parts and ratios are by weight of the total composition, unless otherwise specified. All such weights as they pertain to listed ingredients are based on the specific ingredient level and, therefore, do not include carriers or by-products that may be included in commercially available materials, unless otherwise specified.

I. Skin Treatment Agents

The lotion compositions of the present invention comprise relatively low concentrations of a select combination of skin treatment agents that are capable of reducing and eliminating the occurrence of skin disorders that can result from contact between the skin and moisture-laden air, skin disorders resulting from prolonged moist human tissue that can occur from the skin being exposed to moisture or other body exudates, and/or skin disorders that are generated from contact between the skin and microbial or bacterial agents. The phrase "select combination of body treatment agents" refers to the following combinations: a. hexamidine, zinc oxide, and niacinamide; b. hexamadine and zinc oxide; and c. hexamadine and niacinamide.

Surprisingly, the select combination of body treatment agents can be included at low individual concentrations, relative to their use in the prior art, and still be effective. For example, the lotion compositions of the present invention can include hexamidine at a concentration of about 0.1% or less by weight, zinc oxide at a concentration of about 1% or less by weight, and niacinamide at a concentration of about 2% or less by weight to achieve equal or superior benefits in the prevention and/or treatment of skin disorders as compared to known lotion compositions that generally comprise these skin treatment agents at higher levels. Similarly, the total effective concentration of the select combination of body treatment agents in the compositions of the present invention are also relatively low. The total concentration of the select combination of body treatment agents ranges from about 0.002% to about 10%, preferably from about 0.01% to about 5%, more preferably from about 0.1% to about 2% by weight of the lotion composition.

A. Hexamidine:

The lotion compositions of the present invention comprise hexamidine body treatment agent at concentrations ranging from about 0.001% to about 0.1%, from about 0.005% to about 0.1%, or even from about 0.01% to about 0.1% by weight of the composition. The hexamidine body treatment agent suitable for use herein include those aromatic diamines which generally conform to the following formula:

These aromatic diamines are referred to as 4,4'-[1,6-Hexanediylbis(oxy)]bisbenzenecarboximidamide; 4,4'-(hexamethylenedioxy) dibenzamidine; and 4,4'-diamidino-α,ω-diphenoxyhexane. The most popular employed form of hexamidine is the general category of hexmidine salts, which include acetate, salicylate, lactate, gluconate, tartarate, citrate, phosphate, borate, nitrate, sulfate, and hydrochloride salts of hexamidine. Specific nonlimiting examples of hexamidine salts include hexamidine isethionate, hexamidine diisethionate, hexamidine hydrochloride, hexamidine gluconate, and mixtures thereof. Hexamidine isethionate and hexamidine diisethionate are β-hydroxyethane sulfonate salts of hexamidine which are preferred for use herein as a skin treatment agent in the prevention and/or treatment of skin disorders. Hexamidine diisethionate is the most preferred hexamidine compound suitable for use as the skin treatment agent herein and is available from Laboratories Serolobilogiques (Pulnoy, France) and the Cognis Incorporation (Cincinnati, Ohio) under the tradename ELASTAB HP100.

Hexamidine compounds are known as effective body treatment agents that can control microbial growth that can lead to irritating and itching skin disorders and odor discomfort. Therefore, these skin treatment agents are often referred to as antimicrobial agents. As used herein the term "antimicrobial agents" refer to materials which function to destroy or suppress the growth or metabolism of microbes, and include the general classification of antibacterial, antifungal, antiprotozoal, antiparasitic, and antiviral agents.

It has been found, however, that a low concentration (about 0.1% or less by weight) of hexamidine provides for improved reduction and/or prevention of skin irritating infections, especially when a low amount of hexamidine is combined with a low concentration of other antimicrobial agents such as zinc oxide and/or niacinamide. This combination of hexamidine and zinc oxide and/or niacinamide can be administered topically and internally at a total concentration less than an effective amount of an applied dosage of these individual compounds. As used herein the term "effective amount" refers to an amount with provides a therapeutic benefit with minimal or no adverse reaction in the reduction and/or prevention of any noticeable or unacceptable skin abnormality which causes irritating, acute, or chronic symptoms including itching and inflammation.

Other aromatic diamines are also suitable for use as a skin treatment agent herein. Such compounds include butamidine and derivatives thereof including butamidine isethionate; pentamidine and derivatives thereof including pentamidine isethionate and pentamidine hydrochloride; dibromopropamidine and derivatives thereof including dibromopropamidine isethionate; stilbamidine and derivatives thereof including hydroxystilbamidine, stilbamidine dihydrochloride, and stilbamidine isethionate; diaminodiamidines and derivatives thereof; and mixtures thereof.

B. Zinc Oxide:

The lotion compositions of the present invention comprise zinc oxide body treatment agent at concentrations ranging from about 0.001% to about 10%, preferably from about 0.005% to about 5%, more preferably from about 0.005% to about 2%, most preferably from about 0.01% to about 1% by weight of the composition. The zinc oxide body treatment agent can be included in the compositions as an individual zinc oxide compound or a combination of zinc oxides, provided that the individual or combined zinc oxide can readily combine with the hexamidine and niacinamide body treatment agents to provide antimicrobial benefits.

The zinc oxide body treatment agent suitable for use herein include those inorganic white and yellowish-white powders that conform to the formula ZnO, and that are more fully described in *The Merck Index*, Eleventh Edition, entry 10050, p. 1599 (1989). Some particularly useful forms of zinc oxide include those that are manufactured and commercially available in average particle size diameters that range from about 1 nm (nanometer) to about 10 μm (micrometer), alternatively from about 10 nm to about 1 μm or even from about 20 nm to about 500 nm. Surprisingly, the inventors have discovered that the use of the above mentioned, relatively small nanoparticle diameter size zinc oxide avoids undesirable skin or hair whitening that results from the transfer of the zinc oxide containing emollient from the topsheet of absorbent article to the wearer's body during product use. This is a particular benefit when the product is a panty liner, sanitary napkin, incontinence brief, or other absorbent article intended to be used by adults having hair in the region where the lotion composition will transfer.

Commercially available zinc oxides include the white zinc oxide powders sold under the tradename ULTRAFINE 350 which is commercially available from the Kobo Incorporation located in South Plainfield, N.J. Other suitable zinc oxide materials include a premix of zinc oxide and a dispersing agent such as polyhydroxystearic acid wherein this premix is available from the Uniqema Incorporation (Wilimington, Del.) under the tradename Arlecel® P100; and a premix of zinc oxide and an isononyl isononanoate dispersing agent which is available from the Ikeda Incorporation (Island Park, N.Y.) under the tradename Salacos® 99.

C. Niacinamide:

The lotion compositions of the present invention comprise niacinamide body treatment agent as an individual niacinamide or as a combination of niacinamides at a total niacinamide concentration ranging from about 0.01% to about 10%, preferably from about 0.05% to about 5%, more preferably from about 0.2% to about 2% by weight of the lotion composition. The niacinamide body treatment agent provides for skin conditioning benefits as well as providing for increased efficacy of the body treatment agents in controlling skin disorders.

Nonlimiting examples of niacinamide body treatment agents suitable for use in the lotion compositions of the present invention include those niacinamide compounds that are amide derivatives of nicotinic acid, and that generally conform to the following formula:

Niacinamide and nicotinic acid are also known as Vitamin $B_3$ and Vitamin $B_5$, whereas niacinamide is the commonly used active form. Niacinamide derivatives including salt derivatives are also suitable for use herein as a body treatment agent. Nonlimiting specific examples of suitable niacinamide derivatives include nicotinuric acid and nicotinyl hydroxamic acid.

The niacinamide body treatment agent can also be included in the composition as acidified niacinamide compounds. The process of acidifying niacinamide compounds is within the gambit of those skilled in the art, wherein one such technique involves dissolving niacinamide in an alcohol solution, adding while stirring an equal molar amount of a fatty acid such as stearic acid (e.g., mixing 1 part niacinamide to 2.4 parts stearic acid), and then air drying the mixture until the alcohol evaporates. A suitable stearic acid compound that can be used in the process of acidifying niacinamide is stearic acid sold under the tradename Emersol® 150 which is available from the Cognis Corporation.

Examples of the above niacinamide compounds are well known in the art and are commercially available from a number of sources, for example, the Sigma Chemical Company (St Louis, Mo.); ICN Biomedicals, Incorporation (Irvin, Calif.); Aldrich Chemical Company (Milwaukee, Wis.); and Em Industries HHN (Hawthorne, N.Y.).

D. Optional Components:

Nonlimiting examples of optional suitable body treatment actives useful in the present invention include allantoin; aluminum hydroxide gel; calamine; cysteine hydrochloride; racemic methionine; sodium bicarbonate; Vitamin C and derivatives thereof; protease inhibitors including serine proteases, metalloproteases, cysteine proteases, aspartyl proteases, peptidases, and phenylsulfonyl fluorides; lipases; esterases including diesterases; ureases; amylases; elastases; nucleases; guanidinobenzoic acid and its salts and derivatives; herbal extracts including chamomile; and mixtures thereof. Guanidinobenzoic acid and its salts and derivatives are more fully described in U.S. Pat. No. 5,376,655, issued to Imaki et al. on Dec. 27, 1994. These other suitable skin treatment actives are typically included at concentrations ranging from about 0.001% to about 10% by weight of the lotion composition.

Furthermore, one or more optional components known or otherwise effective for use in lotion compositions may be included provided that the optional components are physically and chemically compatible with the essential body treatment and carrier components, or do not otherwise unduly impair product stability, aesthetics, or performance. Such optional components are typically included at concentrations ranging from about 0.001% to about 20% by weight of the compositions, and include materials such as water, skin conditioning agents, perfumes, deodorants, opacifiers, astringents, preservatives, emulsifying agents, film formers, stabilizers, proteins, lecithin, urea, colloidal oatmeal, pH control agents, and other Monographed materials that are deemed safe by the U.S. Food and Drug Administration (FDA) under 21 C.F.R. §347 for use on human skin. Other optional components for use in the lotion compositions of the present invention include fats or oils, or essential oils. These oils can be present at concentrations ranging from about 0.0001% to 10% by weight of the compositions, and include materials such as Anise Oil, Apricot Kernel Oil, Avocado Oil, Balm Mint Oil, Babassu Oil, Borage Seed Oil, Butter, Bee Balm Oil, Birch Oil, Bitter Almond Oil, Bitter Orange Oil, C10-C18 Triglycerides, C12-C18 Acid Triglyceride, Camellia Oil, *Calendula* Oil, California Nutmeg Oil, Canola Oil, Caprylic/Capric/Lauric Triglyceride, Caprylic/Capric/Linoleic Triglyceride, Caprylic/Capric/Stearic Triglyceride, Caprylic/Capric Triglyceride, Caraway Oil, Carrot Oil, Cashew Nut Oil, Castor Oil, Chamomile Oil, Cherry Pit Oil, Chia Oil, Cinnamon Oil, Cloveleaf Oil, Clove Oil, Cocoa Butter, Coconut Oil, Cod Liver Oil, Coriander Oil, Corn Germ Oil, Corn Oil, Cottonseed Oil, Cypress Oil, Epoxidized Soybean Oil, Evening Primrose Oil, Eucalyptus Oil, Fennel Oil, Gardenia Oil, Geranium Oil, Ginger Oil, Glyceryl Triacetyl Hydroxystearate, Glyceryl Triacetyl Ricinoleate, Glycosphingolipids, Grape Seed Oil, Grapefruit Oil, Hazelnut Oil, Human Placental Lipids, Hybrid Safflower Oil, Hybrid Sunflower Seed Oil, Hydrogenated Castor Oil, Hydrogenated Coconut Oil, Hydrogenated Cottonseed Oil, Hydrogenated C2-C1 Triglycerides, Hydrogenated Fish Oil, Hydrogenated Lard, Hydrogenated Menhaden Oil, Hydrogenated Mink Oil, Hydrogenated Orange Roughy Oil, Hydrogenated Palm Kernel Oil, Hydrogenated Palm Oil, Hydrogenated Peanut Oil, Hydrogenated Shark Liver Oil, Hydrogenated Soybean Oil, Hydrogenated Tallow, Hydrogenated Vegetable Oil, Hyptis Oil, Juniper Oil, Kiwi Oil, Laurel Oil, Lanolin and Lanolin derivatives, Lard, Lauric/Palmitic/Oleic Triglyceride, Lavender Oil, Lemongrass Oil, Lemon Oil, *Lesquerella* Oil, Lovage Oil, *Macadamia* Nut Oil, Maleated Soybean Oil, Mandarin Orange Oil, Meadowfoam Seed Oil, Menhaden Oil, Mink Oil, Moring a Oil, *Mortierella* Oil, Musk Rose Oil, Neatsfoot Oil, Nutmeg Oil, Oleic/Linoleic Triglyceride, Oleic/Paimitic/Lauric/Myristic/Linoleic Triglyceride, Oleostearine, Olibanurn, Olive Husk Oil, Olive Oil, Ornental Lipids, Orange Flower Oil, Orange Oil, Orange Roughy Oil, Palm Kernel Oil, Palm Oil, Peach Kernel Oil, Peanut Oil, Pengawar Djambi Oil, Peppermint Oil, Pentadesma Butter, Phospholipids, Pistachio Nut Oil, Pine Oil, Placental Lipids, Rapeseed Oil, Rice Bran Oil, Rose Hips Oil, Rosemary Oil, Rose Oil, Rue Oil, Safflower Oil, Sage Oil, Sandalwood Oil, Sassafras Oil, Sesame Oil, Shark Liver Oil, Shea Butter, Soybean Oil, Spearmint Oil, Sphingolipids, Sunflower Seed Oil, Sweet Almond Oil, Sweet Marjoram Oil, Sweet Violet Oil, Tall Oil, Tallow, Tea Tree Oil, Thyme Oil, Tribehenin, Tricaprin, Tricaprylin, Triheptanoin, Trihydroxymethoxystearin, Trihydroxystearin, Triisononanoin, Triisostearin, Trilaurin, Trilinolein, Trilinolenin, Trimyristin, Trioctanoin, Triolein, Tripalmitin, Trisebacin, Tristearin, Triundecanoin, Walnut Oil, Wheat Bran Lipids, Wheat Germ Oil, Wild Mint Oil, Yarrow Oil, Ylang Ylang Oil, Zadoary Oil, C10 Fatty Acids: Arachidic Acid, Behenic Acid, Capric Acid, Caproic Acid, Caprylic Acid, Coconut Acid, Corn Acid, Cottonseed Acid, Hydrogenated Coconut Acid, Hydrogenated Menhaden Acid, Hydrogenated Tallow Acid, Hydroxystearic Acid, Isostearic Acid, Lauric Acid, Linoleic Acid, Linolenic Acid, Myristic Acid, Oleic Acid, Palmitic Acid, Palm Kernel Acid, Pelargonic Acid, Ricinoleic Acid, Soy Acid, Stearic Acid, Tallow Acid, Undecanoic Acid, Undecylenic Acid, Wheat Germ Acid, and the like, as well as mixtures thereof. Specific optional lotion conditioning agents found useful in the present invention include panthenol, glycerine, and chamomile oil which are described in detail hereinbelow.

Other optional components known or otherwise effective for use in lotion compositions may also include sterols, phytosterols, and sterol derivatives that act in combination with the natural fats/oils to provide natural skin barrier enhancement and skin barrier recovery. Sterols and sterol derivatives that can be used in the compositions of the invention include, but are not limited to: β-sterols having a tail on the 17 position and having no polar groups for example, cholesterol, sitosterol, stigmasterol, and ergosterol, as well as, C10-C30 cholesterol/lanosterol esters, cholecalciferol, cholesteryl hydroxystearate, cholesteryl isostearate, cholesteryl stearate, 7-dehydrocholesterol, dihydrocholesterol, dihydrocholesteryl octyldecanoate, dihydrolanosterol, dihydrolanosteryl octyldecanoate, ergocalciferol, tall oil sterol, soy sterol acetate, lanasterol, soy sterol, avocado sterols, "AVOCA- DIN" (trade name of Croda Ltd of Parsippany, N.J.), sterol esters and similar compounds, as well as mixtures thereof. A suggested commercially available example of phytosterol is GENEROL 122 N PRL refined soy sterol from Cognis Corporation of Cincinnati, Ohio.

Panthenol:

Where included, panthenol typically comprises from about 0.001% to about 10%, preferably from about 0.005% to about 5%, more preferably from about 0.05% to about 1% by weight of the lotion composition. The optional panthenol body conditioning agent provides for skin emolliency benefits that can leave the body feeling smooth, soothing, and soft during and after interaction of the body tissues with the body treatment agents. The lotion compositions of the present invention can include an individual panthenol compound or a mixture of panthenol compounds.

Nonlimiting examples of panthenol include those panthenol compounds which are alcohol or ester derivatives of pantothenic acid. Pantothenic acid is a member of the B complex family and is often referred to as Vitamin $B_3$. Like pantothenic acid, the panthenol alcohol derivatives of this acid can exist as stereoisomers, for example, the D(+) form, the L(-) form, the racemate, and mixtures of the D(+) and L(-) forms. Specific examples of panthenol include, but are not limited to, D-panthenol (a.k.a. dexpanthenol), and dl-panthenol. Panthenol is more fully described in *The Merck Index*, Eleventh Edition, entry 2924, p. 464 (1989), which description is incorporated herein by reference. Examples of commercially available panthenol include D-panthenol which is available from Roche Vitamins Incorporation (Nutley, N.J.), a subsidiary of F. Hoffman LaRoche, Ltd.

Glycerine:

Where included, the lotion compositions comprise the preferred optional glycerine body conditioning agent at concentrations ranging from about 0.01% to about 10%, preferably from about 0.02% to about 5%, more preferably from about 0.05% to about 2% by weight of the lotion composition. The optional glycerine body conditioning agent also provides for skin emolliency benefits such as smooth, soothing, and soft feeling body, as well as being a dispersing agent for the niacinamide body treatment agent.

Glycerine is a C3 monohydric alcohol that is also referred to as glycerol and 1,2,3-propanetriol. Glycerine derivatives are also suitable for use as an optional skin conditioning agent herein wherein such derivatives include polyglycerols having from about 2 to about 16 repeating glycerol moieties. A specific example of a suitable glycerine skin conditioning agent is Glycerine, USP Kosher® which is commercially available from the Procter & Gamble Company located in Cincinnati, Ohio.

Chamomile:

The lotion compositions comprise the preferred optional chamomile oil at concentrations ranging from about 0.0001% to about 10%, preferably from about 0.001% to about 5%, more preferably from about 0.005% to about 2% by weight of the lotion composition. The optional chamomile oil skin conditioning agent also provides for skin benefits such as soothing. Chamomile oil is commonly prepared as an oil extract of chamomile flowers. An example of a commercially available chamomile oil include Phytoconcentrol Chamomile which is available from Dragoco Incorporation (Totowa, N.J.).

Silk Protein or Silk Amino Acids or Silk Peptides:

Silk protein is composed of silk fiber and sericin. The silk protein is produced by species of the phylum Arthropoda, classes Insecta and Arachnida. Common species include the silkworm and spider. Sericin acts as a protective envelope around the fibroin thread as it is spun and can be easily separated from silk protein by chemical processes such as hydrolysis. Sericin and/or silk amino acids and/or silk peptides are amenable to binding to the skin and hair, forming a resistant, moisturizing, and protective film on the skin/hair. The optional silk also provides for body benefits such as soothing, moisturizing, and conditioning. Another example of a silk derivative for use in the lotion composition of the present invention is a fine powder of silk fibroin in nonfibrous or particulate form, as disclosed in U.S. Pat. No. 4,233,212 to Otoi et al., incorporated herein by reference in its entirety. The lotion compositions comprise the preferred optional silk protein or silk amino acids, or mixtures thereof at concentrations ranging from about 0.0001% to about 25%, preferably from about 0.0005% to about 15%, more preferably from about 0.001% to about 10% by weight of the lotion composition. Silk protein or silk derived amino acids or peptides is commonly prepared as a powder or as part of an aqueous solution. Silk proteins generally have an average molecular weight of >8000 and can have molecular weights of >500.000. Silk amino acid or silk peptide solutions typically have lower molecular weights which may typically be described as between 40 and 400. A commercially available silk protein is available from Croda, Inc., of Parsippany, N.J., and is sold under the trade name CROSILK® LIQUID (silk amino acids), CROSILK® 10,000 (hydrolyzed silk), CROSILK® POWDER (powdered silk), and CROSILKQUAT (cocodimonium hydroxypropyl silk amino acid). Another example of a commercially available silk protein is sericin, available from Pentapharm, LTD, a division of Kordia, by, of the Netherlands. Further details of such silk protein mixtures can be found in U.S. Pat. No. 4,906,460, to Kim, et al., assigned to Sorenco, which is herein incorporated by reference in its entirety. Other sources of silk include Collaborative Laboratories Silkall 100®, Silkpro®, and SilPRO® Silk Essence.

Branched Chain Amino Acids and Enzyme Activator:

The lotion compositions can comprise the preferred optional branched chain amino acids and enzyme activator, or mixtures thereof at a at concentrations ranging from about 0.0001% to about 40%, preferably from about 0.001% to about 30%, more preferably from about 0.001% to about 10% by weight of the lotion composition. Branched chain amino acids are selected from the group leucine, isoleucine, and valine or their derivatives or their metabolites. The enzyme activators are selected from the group consisting of octanoic acid and its derivatives, hexanoic acid and its derivatives, alpha ketoisocaproic acid and its derivatives, thiamin diphosphate and its derivatives and related materials capable of activating the enzyme, branched-chain keto acid dehydrogenase. The amino acid derivatives or metabolites are selected from the group consisting of: nor-leucine, nor-valine, L-alloisoleucine, L-threo-isoleucine, D, L, or DL-leucine-containing di- and tri-peptides, isovaleryl-CoA, isovalerylcarnitine, alpha-methylbutyrylglycine, alpha-methylbutyric acid, and related amino acids and metabolites as described in U.S. Pat. No. 6,149,924 issued to Harbhaj an Paul on Nov. 21, 2000. Leucine, isoleucine, and valine can be obtained under the tradename AEC Leucine, AEC Isoleucine, and AEC Valine, respectfully, from A&E Connock (Hampshire, United Kingdom). Octanoic acid and hexanoic acid can be obtained under the tradename AEC Caprylic Acid and AEC Caproic Acid, respectfully, from A&E Connock (Hampshire, United Kingdom).

Phytosteroids

Phytosteroids represent materials that are extracted from plants. Representative ingredients can include steroidal and non-steroidal structures both possessing steroid-like biological activity. Examples of steroidal materials include vegetable oil derived steroids, i.e., sitosterol, stigmasterol, and campesterol. Non-steroidal structures include isoflavones, flavones, and coumestans. Isoflavones, which include genestein, daidzein, formononetin, and equol have been identified as useful treatments for symptoms associated with menopause and perimenopause (U.S. Pat. No. 5,498,631 to GORBACH Mar. 12, 1996), depression and dementia (U.S. Pat. No. 5,733,926 to GORBACH Mar. 31, 1998, U.S. Pat. No. 6,083,526 to GORBACH, Jul. 4, 2000), skin wrinkling (U.S. Pat. No. 6,060,070 to GORBACH May 9, 2000), and cancer (WO 2004022023 to NOVOGEN). The principal route of delivery is through pills, food, suppositories, cosmetic formulas or, restricted to sun exposed areas of the body (i.e., to treat and prevent solar actinic damage as described in WO 2004026274 to NOVOGEN and WIDYARINI S. ET AL.: 'Isoflavonoid compounds from red clover (*Trifolium pratense*) protect from inflammation and immune suppression induced by UV radiation' PHOTOCHEMISTRY AND PHOTOBIOLOGY vol. 74, no. 3, 2001, pages 465-470.). Since these isoflavones are known to have multiple effects in the body, and to avoid any undesirable side effects, it is critical that the isoflavones be targeted to the tissue/organ of interest at the appropriate dosage and be delivered in a way that will ensure compliance, i.e., what might be appropriate for oral administration will not be the same for topical administration, and what might be appropriate as a cosmetic composition for the face and arms will not be acceptable in the vulvar area, and in particular for an absorbent article. Furthermore, although there is disclosure for delivering isolaflavones through the skin using a skin patch composition (U.S. Pat. No. 6,083,526 to GORBACH, Jul. 4, 2000), it is common knowledge that the adhesives used in skin patches can be irritating to the vulvar skin and be uncomfortable to wear, thus compromising user compliance. There is also disclosure of the use of a combination of isoflavones and microorganisms in mature women to treat symptoms associated with older women (U.S. Pat. No. 6,716,424 to OTSUKA PHARM CO LTD Apr. 6, 2004) or a combination of isoflavones and steroids (US 2004131579A to AVON). By modifying the natural ecoflora found in this heavily colonized part of the body, this treatment would pose significant health risk when applied to the vulvar area. Steroids are well known to carry a systemic health risk.

Thus there is a need to target the delivery of a safe composition of isoflavones to the target skin of interest, there is need to formulate the isoflavones in a carrier to deliver the isoflavones to the target of interest, there is a need to use a device to deliver the isoflavones to the vulvar area, there is a need for the carrier containing isoflavones to be compatible with an absorbent article that is normally used by females and whose carrier containing isoflavones can be transferred to the body the wearer.

The lotion composition can include 0.001% to about 40% of isoflavones, preferably 0.001% to about 4%, more preferably 0.01% to about 0.5% isoflavones. The isoflavones can be selected from the group consisting of soy isoflavones, clover isoflavones, genestein, daidzein, formononetin, biochanin A, S-equol, R-equol or a mimetic plant extract. By mimetic plant extract is meant, in the context of the application, any plant extract capable of mimicking the action of the isoflavones identified.

Plant Extract:

The lotion compositions can comprise the preferred optional plant extract at concentrations ranging from about 0.0001% to about 40%, preferably from about 0.001% to about 20%, more preferably from about 0.001% to about 5% by weight of the lotion composition. The plant extract is obtainable by grinding a whole plant or one or more of plant parts (e.g., leaves, bark, roots, branches, etc.), either dried or undried, and extracting with a solvent at ambient temperature or under heating or by means of an extractor, e.g., a Soxhlet's extractor. Extracted plant (or botanical) actives can include any water-soluble or oil-soluble active extracted from a particular plant. Botanical extracts are generally available from commercial suppliers as part of a composition that also contains an extracting solvent. Amounts of the botanical extract in the compositions of the present invention in terms of active component may range from about 0.000001% (by total weight of the composition) to about 10% (by total weight of the composition). In addition, the botanical extracted actives can be supplied as a powder. Any plant extract can be used with no particular restriction as long as it has no apparent adverse effect on the absorbent article's physical integrity (i.e., dissolves adhesive glues) or substantially no decomposing action on the absorbent core. Examples of botanical extracts include, but are not limited to absinthe, *Agnus castus*, alga (e.g., bladder wrack (*Fucus vesiculosis*)), aloe vera, apple, *Areca catechu*, arnica, basil leaves, bell pepper, *Beta vulgaris* (beet), blackberry, black cohosh, black currant fruit, black tea, blueberry, borage seed *calendula*, carrot root, centella asiatica, chamomile, Chinese tea, chokeberry, Chuck Berry, citron, coffee seed, comfrey, cornflower, crowberry, dandelion root, date palm fruit, dong quad, echinacea, evening primrose, eucalyptus, fenugreek, fennel fruit, field horsetail, gingko, gooseberry, grapefruit fruit, grape seed extract, green tea, hamamelis, hawthorn berries, hiba arborvitae, horse chestnut, *Hypericum pefforatum*, ivy (*Herdera helix*), lavender, lemon balm, licorice, magnolia, mimosa, oat, mung bean, oolong tea, oregano, pansey, peach leaf, persimmon, philodendron, Rhododendron, rosemary, sage, St. John's wort, scullcap, seabuckthorn, strawberry, sweet pea, thyme, tomato, Turkish oregano, vanilla fruit, yucca glauca, white nettle, whortleberry, willow herb, and witch hazel. Another group of botanical extracts include perfume or essential oils.

Examples of essential oils that can be incorporated in the lotion composition include: Anise Oil, Balm Mint Oil, Basil Oil, Bee Balm Oil, Bergamot Oil, Birch Oil, Bitter Almond Oil, Bitter Orange Oil, *Calendula* Oil, California Nutmeg Oil, Caraway Oil, Cardamom Oil, Chamomile Oil, Cinnamon Oil, Clary Oil, Cloveleaf Oil, Clove Oil, Coriander Oil, Cypress Oil, Eucalyptus Oil, Fennel Oil, Gardenia Oil, Geranium Oil, Ginger Oil, Grapefruit Oil, Hops Oil, Hyptis Oil, Indigo Bush Oil, Jasmine Oil, Juniper Oil, Kiwi Oil, Laurel Oil, Lavender Oil, Lemongrass Oil, Lemon Oil, Linden Oil, Lovage Oil, Mandarin Orange Oil, Matricaria Oil, Musk Rose Oil, Nutmeg Oil, Olibanum, Orange Flower Oil, Orange Oil, Patchouli Oil, Pennyroyal Oil, Peppermint Oil, Pine Oil, Pine Tar Oil, Rose Hips Oil, Rosemary Oil, Rose Oil, Rue Oil, Sage Oil, *Sambucus* Oil, Sandalwood Oil, Sassafras Oil, Silver Fir Oil, Spearmint Oil, Sweet Marjoram Oil, Sweet Violet Oil, Tar Oil, Tea Tree Oil, Thyme Oil, Wild Mint Oil, Yarrow Oil, Ylang Ylang Oil, and the like, as well as mixtures thereof. Perfume oils are natural odorous substances that are generally extracted from blossoms (lilly, lavender, rose, jasmine, neroli, ylang-ylang), from stems and leaves (geranium, patchouli, petitgrain), from fruits (anis, coriander, caraway, juniper), from cortex (bergamot, lemon, orange), from roots (macis, angelic, celery, *cardamon, costus*, iris, calmus), from wood (pine, sandelwood, guajak, cedar, rose), from herbs and grass (tarragon, lemongrass, sage, thyme), from needles and branches (spruce, fir, pine, mountain pine), from resins and balms (galbanum, elemi, benzoin, myrrh, olibanum, opoponax).

II. Carrier:

The lotion compositions of the present invention comprise a carrier for the body treatment agents. The carrier can be included in the compositions as an individual carrier or a combination of carrier ingredients, provided that the total carrier concentration is sufficient to provide transfer and/or migration of the body treatment agents onto the body. The carrier can be a liquid, solid, or semisolid carrier material, or a combination of these materials, provided that the resultant carrier forms a homogenous mixture or solution at selected processing temperatures for the resultant carrier system and at processing temperatures for combining the carrier with the skin treatment agents in formulating the lotion compositions herein. Processing temperatures for the carrier system typically range from about 60° C. to about 90° C., more typically from about 70° C. to about 85° C., even more typically from about 70° C. to about 80° C.

The lotion compositions of the present invention typically comprise the carrier at a total carrier concentration ranging from about 60% to about 99.9%, preferably from about 70% to about 98%, more preferably from about 80% to about 97% by weight of the lotion composition. Suitable carrier compounds include petroleum-based hydrocarbons having from about 4 to about 32 carbon atoms, fatty alcohols having from about 12 to about 24 carbon atoms, polysiloxane compounds, fatty acid esters, alkyl ethoxylates, lower alcohols having from about 1 to about 6 carbon atoms, low molecular weight glycols and polyols, fatty alcohol ethers having from about 12 to about 28 carbon atoms in their fatty chain, lanolin and its derivatives, glyceride and its derivatives including acetoglycerides and ethoxylated glycerides of C12-C28 fatty acids, and mixtures thereof. Alternatively or in combination with, the carrier may also be composed of polysiloxane compounds non-limiting examples include dimethicones (1-100,000,000 centistoke), cyclomethicones, alkylated silicones (hair conditioning agents), silicone gums, silicone gels, silicone waxes, copolymers of silicone (vinyl dimethicone polymers, phenyl vinyl dimethicone polymers, alkylated silicone polymers, polyethylene oxide/silicone copolymers, polyethylene oxide/alkyl silicone copolymers), and mixtures thereof.

Nonlimiting examples of suitable petroleum-based hydrocarbons having from about 4 to about 32 carbon atoms include mineral oil, petrolatum, isoparaffins, various other branched chained hydrocarbons, and combinations thereof. Mineral oil is also known as "liquid petrolatum", and usually refers to less viscous mixtures of hydrocarbons having from about 16 to about 20 carbon atoms. Petrolatum is also known as "mineral wax", "petroleum jelly", and "mineral jelly", and usually refers to more viscous mixtures of hydrocarbons having from about 16 to about 32 carbon atoms. An example of commercially available petrolatum include petrolatum sold as Protopet® 1S which is available from the Witco Corporation located in Greenwich, Conn.

Nonlimiting examples of suitable fatty alcohols having from about 12 to about 24 carbon atoms include saturated, unsubstituted, monohydric alcohols or combinations thereof, which have a melting point less than about 110° C., preferably from about 45° C. to about 110° C. Specific examples of fatty alcohol carriers for use in the lotion compositions of the present invention include, but are not limited to, cetyl alcohol, stearyl alcohol, cetearyl alcohol, behenyl alcohol, arachidyl alcohol, lignocaryl alcohol, and combinations thereof. Examples of commercially available cetearyl alcohol is Stenol 1822 and behenyl alcohol is Lanette 22, both of which are available from the Cognis Corporation located in Cincinnati, Ohio.

Nonlimiting examples of suitable fatty acid esters include those fatty acid esters derived from a mixture of $C_{12}$-$C_{28}$ fatty acids and short chain ($C_1$-$C_8$, preferably $C_1$-$C_3$) monohydric alcohols preferably from a mixture of $C_{16}$-$C_{24}$ saturated fatty acids and short chain ($C_1$-$C_8$, preferably $C_1$-$C_3$) monohydric alcohols. Representative examples of such esters include methyl palmitate, methyl stearate, isopropyl laurate, isopropyl myristate, isopropyl palmitate, ethylhexyl palmitate, and mixtures thereof. Suitable fatty acid esters can also be derived from esters of longer chain fatty alcohols ($C_{12}$-$C_{28}$, preferably $C_{12}$-$C_{16}$) and shorter chain fatty acids such as lactic acid, specific examples of which include lauryl lactate and cetyl lactate.

Nonlimiting examples of suitable alkyl ethoxylates include $C_{12}$-$C_{22}$ fatty alcohol ethoxylates having an average degree of ethoxylation of from about 2 to about 30. Nonlimiting examples of suitable lower alcohols having from about 1 to about 6 carbon atoms include ethanol, isopropanol, butanediol, 1,2,4-butanetriol, 1,2 hexanediol, ether propanol, and mixtures thereof. Nonlimiting examples of suitable low molecular weight glycols and polyols include ethylene glycol, polyethylene glycol (e.g., Molecular Weight 200-600 g/mole), butylene glycol, propylene glycol, polypropylene glycol (e.g., Molecular Weight 425-2025 g/mole) and mixtures thereof. A more detailed description of carrier ingredients including suitable hydrocarbons, polysiloxane compounds, and fatty alcohol ethoxylates can be found in U.S. Pat. No. 5,643,588, issued Jul. 1, 1997 to Roe et al. entitled "Diaper Having A Lotioned Topsheet".

In one embodiment, the carrier comprises a combination of one or more petroleum-based hydrocarbons and one or more fatty alcohols described hereinabove. When one or more petroleum-based hydrocarbons having from about 4 to about 32 carbon atoms are used in combination with one or more fatty alcohols having from about 12 to about 22 carbon atoms, the petroleum-based hydrocarbons are included at total concentrations ranging from about 20% to about 99%, preferably from about 30% to about 85%, more preferably from about 40% to about 80% by weight of the lotion composition; wherein the fatty alcohols are included at total concentrations ranging from about 0.2% to about 65%, preferably from about 1% to about 50%, more preferably from about 2% to about 40% by weight of the lotion composition.

It is believed that a petroleum-based carrier system comprising $C_4$-$C_{32}$ hydrocarbons, $C_{12}$-$C_{22}$ fatty alcohols, and fumed silica provides a homogeneous mixture of the carrier, skin treatment agents, and any optional ingredients wherein this homogeneous mixture ensures sufficient contact between the skin and skin treatment agents to result in effective prevention and treatment of skin disorders. The fumed silica suitable for inclusion in the preferred petroleum-based carrier system, or with any other carrier described herein, includes colloidal pyrogenic silica pigments which are sold under the Cab-O—Sil® tradename, and which are commercially available from the Cabot Corporation located in Tuscola, Ill. These colloidal pyrogenic silica pigments are submicroscopic particulated pyrogenic silica pigments having mean particle sizes ranging from about 0.1 microns to about 100 microns. Specific examples of commercially available Cab-O—Sil® silica pigments include Cab-O—Sil® TS-720 (a polydimethylsiloxane treated fumed silica), Cab-O—Sil® TS-530 (a trimethyl silanized fumed silica), and Cab-O—Sil® TS-610 (a dimethyldisilanized fumed silica). The fumed silica provides the lotion compositions with desired viscosity or thickening properties, and is typically included at concentrations ranging from about 0.01% to about 15%, preferably from about 0.1% to about 10%, more preferably from about 1% to about 5% by weight of the lotion composition.

The fumed silica can be used alone or in combination with other optional viscosity, thickening, or immobilizing agents such as talc, bentonites including treated bentonites, hectorites including treated hectorites, calcium silicates including treated calcium silicates, magnesium silicates, magnesium aluminum silicates, zinc stearates, sorbitol, colloidal silicone dioxides, spermaceti, carnuba wax, beeswax, candelilla wax, paraffin wax, microcrystalline wax, castrol wax, ceresin, esparto, ouricuri, rezowax, polyethylene wax, $C_{12}$-$C_{24}$ fatty acids, polyhydroxy fatty acid esters, polyhydroxy fatty acid amides, polymethacrylate polymers, polymethacrylate and styrene copolymers, and combinations thereof. These other optional viscosity modifying or thickening or immobilizing agents are also included at total concentrations ranging from about 0.01% to about 15% by weight of the lotion composition. A nonlimiting specific example of another suitable viscosity or thickening agent include bentonite sold as Bentone® 38 which is available from the Rheox Incorporation.

Other non-limiting examples of suitable immobilizing agents include natural or synthetic waxes. As used herein, the term 'wax' refers to oil soluble materials that have a waxy constituency and have a melting point or range of above ambient temperature, in particular above 25° C. Waxes are materials that have a solid to semi-solid (creamy) consistency, crystalline or not, being of relative low viscosity a little above their liquefying point. Waxes can be composed of one or more components, synthetic as well as natural, and can in principle be composed of or comprise any oil soluble material having a waxy constituency, including mixtures thereof. Suitable waxes which can be incorporated into the lotion include: beeswax, candelilla wax, carnauba wax, ceresine wax, cocoa butter, cork wax, esparto gras wax, fruit-derived waxes, such as bayberry wax, orange wax, lemon wax, grapefruit wax and bayberry wax, and the like, Guaruma wax, hydrogenated jojoba waxes, hydrogenated microcrystalline wax, hydrogenated rice bran wax, japan wax, jojoba wax, lanolin wax, mineral waxes such as ceresine ouricury, and ozokerite waxes, mink wax, montan wax, motan acid wax, motan wax, paraffin, PEG-6 beeswax, PEG-8 beeswax, polyalkylene and polyethyleneglycol waxes, rezowax, rice bran wax, rice shoot wax, Sasol waxes, shellac wax, spent grain wax, spermateci, sugar cane wax, sunflower wax, synthetic beeswax, synthetic candelilla wax, synthetic carnuba wax, synthetic japan wax, synthetic jojoba wax, wool wax, waxes based on chlorinated naphtalenes such as 'Halowax', It is preferable that the carrier be hydrophobic. Further, it is preferable that the lotion composition of the present invention comprise no surfactant. Therefore, in a preferred embodiment of the present invention the lotion has a level of hydrophobicity at least as great as that of the topsheet, and the hydrophobicity of the lotion is primarily due to the lack of a surfactant component. If, under some condition, there is a need to raise the wettability of the hydrophobic carrier one may optionally add a wetting agent such as polyoxyethylene alkyl ethers, alkyl ethoxylates, alkylethoxylated amines, polyethylene glycol esters, and/or sorbitan fatty acid esters generally having a low degree of ethoxylation and HLB values below about 7. Suitable additives will be miscible with the carrier so as to form a homogenous mixture. Because of possible skin sensitivity of those using the catamenial device of the present invention, these wetting agents should also be relatively mild and non-irritating to the skin. Typically, these wetting agents are nonionic to be not only non-irritating to the skin, but also to avoid other undesirable effects on any underlying tissue laminate structure, e.g., reductions in tensile strength. Suitable wetting agents will typically have HLB values below 10, preferably below 9, more preferably below 8, and even more preferably below 7.

Non-limiting specific examples of a suitable wetting agents includes nonyl phenol or polyoxyethylene nonyl phenyl ether (20 of ethoxylation; HLB of 5.7), octyl phenol or polyoxyethylene octyl phenyl ether (10 of ethoxylation; HLB of 3.5), stearyl alcohol or polyoxyethylene stearyl ether (20 of ethoxylation; HLB of 4.9), stearyl amine or polyoxyethylene stearyl amine (20 of ethoxylation; HLB of 4.9), polyethylene glycol 200 dilaurate (HLB 5.9), polyethylene glycol 200 distearate (HLB 4.8), sorbitan monostearate ('Span 60' having HLB 4.7), sorbitan tristearate ('Span 65' having HLB 2.1), sorbitan monooleate ('Span 80' having HLB 4.3), sorbitan trioleate ('Span 85' having HLB 1.8), each of which are available form Cell Chemical Company (Inchon, Korea) or Uniqema (New Castle, Del., USA).

The amount of wetting agent required to increase the wettability of the lotion composition to a desired level will depend upon its HLB value and HLB level of the carrier used, and like factors. The lotion composition can comprise from about 1 to about 50% of the wetting agent when needed to increase the wettability properties of the composition. Preferably, the lotion composition comprises from about 1 to about 25%, most preferably from about 10 to about 20%, of the wetting agent when needed to increase wettability.

III. Absorbent Article

The lotion compositions of the present invention are preferably transferred to the body from application of the compositions onto a catamenial device. These products may comprise a topsheet, a backsheet, and an absorbent core positioned between the topsheet and backsheet; each component having a body- or wearer-contacting surface and a garment surface. The terms "body-contacting surface" and "wearer-contacting surface" are used interchangeably herein and refer to one or more surfaces of any article component that is intended to be worn or positioned toward or adjacent the body of the wearer/user for contact between the wearer/user and the article's surface at some time during the use period. The term "garment surface" as used herein refers to the outer or exterior surface of any article component that is intended to be worn or positioned adjacent a wearer's undergarments, or in the case of an absorbent article which is not worn by the user, the garment surface is typically positioned adjacent a user's hand or other implement assisting in the use of the absorbent article. As used herein, the term "wearer" and "user" are used interchangeably as the present invention contemplates absorbent articles which may not be intended to be worn, but rather used to absorb bodily exudates while transferring the lotion compositions of the present invention.

A. Topsheet:

The absorbent article may comprise any known or otherwise effective topsheet, such as one which is compliant, soft feeling, and non-irritating to the wearer's body. Suitable topsheet materials include a liquid pervious material that is oriented towards and contacts the body of the wearer permitting bodily discharges to rapidly penetrate through it without allowing fluid to flow back through the topsheet to the skin of the wearer. The topsheet, while being capable of allowing rapid transfer of fluid through it, also provides for the transfer or migration of the lotion composition onto an external or internal portion of a wearer's body. A suitable topsheet can be made of various materials such as woven and nonwoven materials; apertured film materials including apertured formed thermoplastic films, apertured plastic films, and fiber-entangled apertured films; hydro-formed thermoplastic films;

porous foams; reticulated foams; reticulated thermoplastic films; thermoplastic scrims; or combinations thereof, as is well known in the art of making catamenial products such as sanitary napkins, pantiliners, incontinence pads, and the like.

When the topsheet comprises a nonwoven fibrous material in the form of a nonwoven web, the nonwoven web may be produced by any known procedure for making nonwoven webs, nonlimiting examples of which include spunbonding, carding, wet-laid, air-laid, meltblown, needle-punching, mechanical entangling, thermo-mechanical entangling, and hydroentangling.

B. Backsheet:

The catamenial device of the present invention also comprises a backsheet. The backsheet can be any known or otherwise effective backsheet material, provided that the backsheet prevents external leakage of exudates absorbed and contained in the catamenial device. Flexible materials suitable for use as the backsheet include, but are not limited to, woven and nonwoven materials, laminated tissue, polymeric films such as thermoplastic films of polyethylene and/or polypropylene, composite materials such as a film-coated nonwoven material, or combinations thereof, as is well known in the art of making catamenial products such as sanitary napkins, pantiliners, incontinence pads, and the like.

C. Absorbent Core:

The catamenial device also comprises an absorbent. The absorbent core is typically positioned between the topsheet and the backsheet. As used herein, the term "absorbent core" refers to a material or combination of materials suitable for absorbing, distributing, and storing aqueous fluids such as urine, blood, menses, and water found in body exudates. The size and shape of the absorbent core can be altered to meet absorbent capacity requirements, and to provide comfort to the wearer/user. The absorbent core suitable for use in the present invention can be any liquid-absorbent material known in the art for use in absorbent articles, provided that the liquid-absorbent material can be configured or constructed to meet absorbent capacity requirements. Nonlimiting examples of liquid-absorbent materials suitable for use as the absorbent core include comminuted wood pulp which is generally referred to as airfelt; creped cellulose wadding; absorbent gelling materials including superabsorbent polymers such as hydrogel-forming polymeric gelling agents; chemically stiffened, modified, or cross-linked cellulose fibers; meltblown polymers including coform; synthetic fibers including crimped polyester fibers; tissue including tissue wraps and tissue laminates; capillary channel fibers; absorbent foams; absorbent sponges; synthetic staple fibers; peat moss; or any equivalent material; or combinations thereof, as is well known in the art of making catamenial products such as sanitary napkins, pantiliners, incontinence pads, and the like.

IV. Methods of Treating the Body:

The present invention also relates to methods of treating the body with the lotion compositions described herein. Generally, a safe and effective amount of the lotion composition is applied to an absorbent article described herein wherein such safe and effective amounts include applying from about 0.0015 mg/cm$^2$ (0.01 mg/in$^2$) to about 100.5 mg/cm$^2$ (100 mg/in$^2$), preferably from about 0.003 mg/cm$^2$ (0.02 mg/in$^2$) to about 12.4 mg/cm$^2$ (80 mg/in$^2$), more preferably from about 0.02 mg/cm$^2$ (0.015 mg/in$^2$) to about 7.75 mg/cm$^2$ (50 mg/in$^2$), of the lotion composition to the absorbent article.

Typically, a safe and effective amount of the lotion compositions of the present invention is applied to an absorbent article such that at least about 0.00015 mg/cm$^2$ (0.001 mg/in$^2$) to about 15.5 mg/cm$^2$ (100 mg/in$^2$), preferably from about 0.0006 mg/cm$^2$ (0.004 mg/in$^2$) to about 11 mg/cm$^2$ (72 mg/in$^2$), more preferably from about 0.005 mg/cm$^2$ (0.03 mg/in$^2$) to about 6.2 mg/cm$^2$ (40 mg/in$^2$), of the composition is transferred to the body during a single use of an absorbent article which is typically about a three hour period. Absorbent articles are generally changed every three to six hours during the day and once for overnight protection, resulting in at least a safe and effective amount of from about 0.00045 mg/cm$^2$ (0.003 mg/in$^2$) to about 124 mg/cm$^2$ (800 mg/in$^2$), preferably from about 0.0018 mg/cm$^2$ (0.012 mg/in$^2$) to about 88 mg/cm$^2$ (576 mg/in$^2$), more preferably from about 0.015 mg/cm$^2$ (0.09 mg/in$^2$) to about 49.6 mg/cm$^2$ (320 mg/in$^2$), of the lotion composition being administered within a one day interval (24 hour period). However, the transfer of the lotion compositions of the present invention onto a wearer's body via an absorbent article described herein can occur for one day, several days, weeks, months, or years at appropriate intervals provided that safe and effective amounts of the lotion compositions are administered to deliver the body treatment benefits described herein.

The lotion compositions of the present invention can be applied to the absorbent articles by any known or otherwise effective technique for distributing a lotion composition onto an absorbent product such as a disposable absorbent article. Nonlimiting examples of methods of applying the lotion compositions onto an absorbent article include spraying, printing (e.g., flexographic printing), coating (e.g., contact slot coating and gravure coating), extrusion, or combinations of these application techniques. The application of the lotion compositions onto an absorbent article facilitates the transfer or migration of the lotion compositions onto the skin for administration and/or deposition of the lotion compositions, resulting in a safe and effective amount of the compositions being applied for improved prevention and reduction of skin disorders. Therefore, the safe and effective amount of the lotion composition that will transfer or migrate to the body will depend on factors such as the type of lotion composition that is applied, the portion of the body contacting surface where the lotion composition is applied, and the type of absorbent article used to administer the lotion composition.

Any suitable method can be used in determining the amount of a lotion composition described herein that is transferred to the body of a wearer during use of an absorbent article containing the composition. An example of specific methods for the calculation of transfer amounts of lotion compositions include Gas Chromatographic and other quantitative analytical procedures that involve the analysis of in vivo skin analog materials. A suitable Gas Chromatographic procedure is more fully described in WO 99/45973, Donald C. Roe et al, published Sep. 16, 1999.

V. Method of Manufacture:

The lotion compositions of the present invention may be prepared by any known or otherwise effective technique, suitable for providing a lotion composition comprising the essential skin treatment agents defined herein. In general, the lotion compositions are prepared by first making a carrier system comprising suitable carriers such as petrolatum and behenyl alcohol in combination with a fumed silica thickening agent. Next, a mixture comprising the skin treatment agents and any optional ingredients such as optional skin conditioning agents are added to the carrier system at a melt mix temperature of about 80° C. Although the carrier system, skin treatment agents, and any optional ingredients are typically processed at a temperature of about 80° C., these materials can be processed at temperatures ranging from about 60° C. to about 90° C., preferably from about 70° C. to about 90° C. The resultant lotion composition is subsequently applied to a topsheet component of an absorbent article using a contact applicator such as a Nordsen EP 11-12-02.

The lotion compositions of the present invention are prepared such that the compositions can be applied to an absorbent article to result in safe and effective amounts of the compositions being transferred onto the skin of a wearer of the absorbent article. Therefore, the lotion compositions preferably have a product consistency such that they are relatively immobile and localized on the wearer-contacting surface of the absorbent article at ambient conditions, are readily transferable to the wearer at body temperature, and yet are not completely liquid under extreme storage conditions. In other words, the lotion compositions are solids or semisolids at ambient conditions (about 25° C.) and/or body temperature (about 37° C.) so that the compositions are easily transferred onto the skin by way of normal contact, wearer motion, and/or body heat. The consistency of the lotion compositions can be measured according to ASTM D5 test method which involves the use of a penetrometer to measure consistency. Typically, the lotion compositions of the present invention have a consistency of from about 10 to about 300, preferably from about 20 to about 250, more preferably from about 30 to about 200, as measured at 40° C. according to the test procedure outlined in ASTM D5 test method.

The solid or semisolid consistency of the lotion compositions provide for relatively low levels of the compositions to be applied to the absorbent articles to impart the desired lotion benefits. By "semisolid" is meant that the compositions have a rheology typical of pseudoplastic or plastic liquids such that the compositions remain relatively stationary in a desired location on the absorbent article, and do not have a tendency to flow or migrate to undesired locations of the article. The solid lotion compositions of the present invention likewise can remain in a particular location and not flow or migrate to undesired locations of the article. These solid and semisolid lotion compositions have viscosities high enough to keep the compositions localized on an intended location of the article, but not so high as to impede transfer to the wearer's skin Typically, final products of solid and semisolid lotion compositions have viscosities ranging from about $1.0\times10^6$ centipoise to about $1.0\times10^{10}$ centipoise under shear stress conditions of about $3\times10^3$ dynes/cm$^2$ at 40° C. (the shear stress applied to the compositions while the absorbent article is in storage or transported at temperature conditions of about 40° C.).

However, the solid and semisolid lotion compositions can be made flowable for transfer or migration of the compositions onto the skin by applying shear stress that results in deformation of the compositions. The shear stress applied at least once during wear of the absorbent article under temperature conditions of about 40° C. is typically at about $1.0\times10^6$ dynes/cm$^2$, and this shear stress can result in the lotion compositions having a viscosity of from about $1.0\times10^1$ centipoise to about $1.0\times10^5$ centipoise. It is believed that the lotion compositions achieve the lower viscosity values under applied shear stress due to the fact that, while the compositions contain solid components, they also contain liquid materials. During wear of an absorbent article described herein, it is desirable to achieve a low viscosity for obtaining sufficient lubrication between the wearer's skin and the body contacting surface of the article to result in effective transfer of the lotion composition onto the wearer's skin. Viscosity at various shear stress can be measured using rheometers known in the art such as the Rheometer SR-2000 available from Rheometrics Incorporation.

The lotion compositions are typically applied to the topsheet of an absorbent article for delivery of the lotion composition onto an external or internal surface of the body. The lotion composition can be applied to other areas of the absorbent article wherein these areas include wings, side panels, the absorbent core, any secondary layer intermediate the core and topsheet, or any other region of the absorbent article.

Processes for assembling absorbent articles such as the disposable absorbent articles described herein include conventional techniques known in the art for constructing and configuring disposable absorbent articles. For example, the backsheet and/or the topsheet can be joined to the absorbent core or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031.

The lotion compositions of the present invention can also be delivered onto the skin by incorporating the compositions into aerosol dispensers, trigger spray dispensers, pump spray dispensers, jars, stick dispensers, cotton balls, patches, sponges, and any other type of known or otherwise effective delivery vehicle.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. All exemplified concentrations are weight-weight percents, unless otherwise specified.

Example I

The compositions exemplified hereinbelow in Table 1 are representative of carrier systems of the lotion compositions of the present invention. The carrier systems are generally prepared by combining, by weight, petrolatum and a fatty alcohol such as behenyl alcohol, and then heating the mixture while stirring to a temperature of about 80° C. using a low speed propeller mixer. Next, viscosity or thickening agents are added to the mixture to shear mix the ingredients into a final carrier system. Suitable viscosity or thickening agents include beheneth-10, fumed silica, bentonite, and steareth-2, wherein the viscosity or thickening agents are used alone or in combination. The ingredients can be shear mixed at 11,000 revolutions per minute (rpm) using an IKA Ultra Turrax Shear Mixer.

Alternatively, the petrolatum, fatty alcohol, and viscosity or thickening agent can be combined, heated with stirring at 80° C. to melt the ingredients, and then mixed into a final carrier system using a high speed blade mixer such as the Tokusyu Kika TK Robo Mics which operates at 5,000 rpm.

TABLE 1

Carrier Systems

| Component | Sample 1 (Wt. %) | Sample 2 (Wt. %) | Sample 3 (Wt. %) | Sample 4 (Wt. %) | Sample 5 (Wt. %) |
|---|---|---|---|---|---|
| Petrolatum[1] | 80.4 | 78.1 | 70.0 | 70.0 | 80 |
| Behenyl Alcohol[2] | 11.0 | 8.7 | — | 20.0 | 10 |
| Cetearyl Alcohol[3] | | | 30.0 | — | |

TABLE 1-continued

| | Carrier Systems | | | | |
|---|---|---|---|---|---|
| Component | Sample 1 (Wt. %) | Sample 2 (Wt. %) | Sample 3 (Wt. %) | Sample 4 (Wt. %) | Sample 5 (Wt. %) |
| Beheneth-10[4] | — | 10.0 | — | — | — |
| Fumed Silica[5] | 3.6 | 3.2 | — | — | 3.5 |
| Bentonite[6] | — | — | — | 10.0 | — |
| Span 60[7] | — | — | — | — | 6.5 |
| Polypropylene Glycol[8] | 5.0 | — | — | — | — |

Wt. % - weight percent
[1]petrolatum available as Protopet ® 1S from the Witco Corporation
[2]behenyl alcohol available as Lanette 22 from the Cognis Corporation
[3]cetearyl alcohol available as Stenol 1822 from the Cognis Corporation
[4]beheneth-10 available as Mergital ® B10 from the Cognis Corporation
[5]fumed silica available as Cabosil ® TS-720 from the Cabot Corporation
[6]bentonite available as Bentone ® 38 from the Rheox Incorporation
[7]steareth-2 available as Brij ® 762 from the Uniqema Corporation
[8]polypropylene glycol Mn 3,500 from Sigma Aldrich #202355.

Examples II-IX

The following Examples II-IX illustrated hereinbelow in Table 2 are representative of lotion compositions of the present invention that include the carrier systems identified in Table 1. The lotion compositions are prepared by formulating a premix solution of the zinc oxide skin treatment agent and adding the zinc oxide premix to the other skin treatment agents and any optional ingredients such as panthenol and glycerin, or by formulating a skin treatment solution of hexamidine and niacinamide skin treatment agents and any optional ingredients. The skin treatment solution is then added to a carrier system such as those described in Table 1, wherein the skin treatment solution and carrier system is heated while stirring to a temperature of about 80° C. All ingredients are included by weight of the lotion compositions. These lotion compositions are especially effective in the control of skin disorders such as skin erythema, malodor, and skin bacterial infections.

The lotion composition of Example II is subsequently applied to the entire wearer-contacting surface of a DRI-WEAVE topsheet of a sanitary pad product such as Allways Wing Regular Long manufactured by the Procter & Gamble Company. To deliver a safe and effective amount of the lotion composition onto the skin, about 0.4 mg/cm$^2$ (2.6 mg/in$^2$) of the lotion composition is applied to the topsheet using a Meltex EP45 hot melt applicator having a head operating temperature of about 90° C.

The lotion composition of Example III is subsequently applied by spraying the composition onto the entire wearer-contacting surface of a DRI-WEAVE topsheet of a sanitary pad product such as Envive Miniform manufactured by the Procter & Gamble Company. To deliver a safe and effective amount of the lotion composition onto the skin, about 4.0 mg/cm$^2$ (25.8 mg/in$^2$) of the lotion composition is applied to the topsheet using a hot melt pneumatic Dynatec E84B 1758 spray head having a head operating temperature of about 90° C. and an atomization pressure of about 16 kiloPascals (kPa).

The lotion composition of Example IV is subsequently applied by slot coating (Nordsen EP 11-12-02) striped configurations of the composition onto the wearer-contacting surface of a hydrophobic spunbond bicomponent polyethylene/polypropylene topsheet (BBA, Washougal, Wash.) of a sanitary pad product. To deliver a safe and effective amount of the lotion composition onto the skin, the lotion composition is applied to the topsheet in a striped configuration wherein the striped configuration comprises at least two stripes each being 40 millimeters (mm) wide×200 mm long and having about 0.8 mg/cm$^2$ (5.2 mg/in$^2$) of the composition applied thereon.

The lotion composition of Example V is subsequently applied by spraying striped configurations of the composition onto the wearer-contacting surface of a DRI-WEAVE topsheet of a panty liner product such as Alldays Regular manufactured by the Procter & Gamble Company. To deliver a safe and effective amount of the lotion composition onto the skin, the lotion composition is applied to the topsheet in a striped configuration wherein the striped configuration comprises at least two stripes each being 40 millimeters (mm) wide×200

TABLE 2

| | Lotion Compositions | | | | | | | | | | |
|---|---|---|---|---|---|---|---|---|---|---|---|
| Component | Ex. II (Wt %) | Ex. III (Wt %) | Ex. IV (Wt %) | Ex. V (Wt %) | Ex. VI (Wt %) | Ex. VII (Wt %) | Ex. VIII (Wt %) | Ex IX (Wt %) | EX X (Wt %) | EX XI (Wt %) | EX XII (Wt %) |
| Sample 1 | 97.1 | 98.1 | 89.8 | — | — | — | — | — | 98.0 | — | 98.0 |
| Sample 2 | — | — | — | 96.2 | 99.7 | — | — | — | — | — | — |
| Sample 3 | — | — | — | — | — | 95.7 | — | — | — | — | — |
| Sample 4 | — | — | — | — | — | — | 97.3 | — | — | — | — |
| Sample 5 | — | — | — | — | — | — | — | 97.8 | — | 97.4 | — |
| ZnO Premix[8] | 0.7 | 0.2 | 7.1 | 0.75 | 0.2 | — | — | — | 1.48 | 2.5 | — |
| Hexamidine[9] | 0.1 | 0.1 | 0.1 | 0.05 | 0.1 | 0.1 | 0.05 | 0.1 | — | — | — |
| Panthenol[10] | 0.5 | 0.5 | 0.5 | 0.5 | — | 0.5 | 0.25 | — | — | — | — |
| Glycerine[11] | 0.1 | 0.1 | — | — | — | — | — | 0.1 | — | — | — |
| Niacinamide[12] | 1.0 | 1.0 | 2.0 | 2.0 | — | — | — | 2.0 | — | — | — |
| Acidified Niacinamide[13] | — | — | — | — | — | 3.7 | 1.9 | — | — | — | — |
| Chamomile[14] | 0.5 | — | 0.5 | 0.5 | — | — | 0.5 | — | 0.5 | — | — |
| Silk[15] | — | — | — | — | — | — | — | — | 0.02 | 0.1 | 2.0 |

[8]Zinc oxide premix comprising 70% zinc oxide mixture of ULTRAFINE 350 zinc oxide available from the Kobo Incorporation, Arlecel ® P100 available from the Uniqema Incorporation, and Salacos ® 99 available from the Ikeda Incorporation
[9]hexamidine available as hexamidine diisethionate from Laboratories Serolobilogiques under the tradename ELASTAB HP100
[10]panthenol available as D-panthenol from Roche Vitamins Incorporation
[11]glycerine available as Glycerine, USP Kosher ® from the Procter & Gamble Company
[12]niacinamide available from Em Industries HHN
[13]acidified niacinamide made by reacting niacinamide with stearic acid
[14]chamomile available as Phytoconcentrol Chamomile from Dragoco
[15]Silk Protein CROSILK ® from Croda, Inc., of Parsippany, N.J mm long and having about 0.6 mg/cm² (3.9 mg/in²) of the composition applied thereon. The lotion composition is applied to the topsheet using a hot melt pneumatic Dynatec E84B1758 spray head having a head operating temperature of about 90° C. and an atomization pressure of about 16 kiloPascals (kPa).

The lotion composition of Example VI is subsequently applied to the entire wearer-contacting surface of a DRI-WEAVE topsheet of a panty liner product such as Alldays Regular manufactured by the Procter & Gamble Company. To deliver a safe and effective amount of the lotion composition onto the skin, about 0.2 mg/cm² (1.3 mg/in²) of the lotion composition is applied to the topsheet using a Meltex EP45 hot melt applicator having a head operating temperature of about 90° C.

The lotion composition of Example VII is subsequently applied by spraying the composition onto the entire wearer-contacting surface of a DRI-WEAVE topsheet of sanitary pad product such as Envive Miniform manufactured by the Procter & Gamble Company. To deliver a safe and effective amount of the lotion composition onto the skin, about 1.0 mg/cm² (6.5 mg/in²) of the lotion composition is applied to the topsheet using a hot melt pneumatic Dynatec E84B1758 spray head having a head operating temperature of about 90° C. and an atomization pressure of about 16 kiloPascals (kPa).

The lotion composition of Example VIII is subsequently applied to the entire wearer-contacting surface of a DRI-WEAVE topsheet of a panty liner product such as Alldays Regular manufactured by the Procter & Gamble Company. To deliver a safe and effective amount of the lotion composition onto the skin, about 0.4 mg/cm² (2.6 mg/in²) of the lotion composition is applied to the topsheet using a Meltex EP45 hot melt applicator having a head operating temperature of about 90° C.

The lotion composition of Example IX is subsequently applied by slot coating (Nordsen EP 11-12-02) striped configurations of the composition onto the wearer-contacting surface of a hydrophobic spunbond bicomponent polyethylene/polypropylene topsheet (BBA, Washougal, Wash.) of a sanitary pad product. To deliver a safe and effective amount of the lotion composition onto the skin, about 3.0 mg/cm² (19.5 mg/in²) of the lotion composition is applied to the topsheet.

For catamenial devices the amount of lotion add on level can be significantly higher that that used in other absorbent articles, such as diapers. For example, while not being bound by theory, it is believed that lotion can be added on at levels of 3 mg/cm², 4 mg/cm², 5 mg/cm², 6 mg/cm², 7 mg/cm², 8 mg/cm², 9 mg/cm², or 10 mg/cm². These levels refer to the area actually covered by lotion.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A catamenial device comprising:
   A) a liquid pervious topsheet, said topsheet having an inner surface oriented toward the interior of said absorbent article and an outer surface oriented toward the skin of the wearer when said absorbent article is being worn, wherein at least a portion of said topsheet outer surface comprises an effective amount of a lotion coating which is semi-solid or solid at 25° C. and which is partially transferable to the wearer's body, said lotion coating comprising:
      (i) from 60 to 99.9% of a carrier comprising a petroleum based hydrocarbon and lower molecular weight glycols or polyols,
      (ii) from 0.2 to 65% of a fatty alcohol with a melting point from 45° C. to 110° C., and
      (iii) from 0.001 to 40% of an isoflavone;
   B) a backsheet joined to said topsheet; and
   C) an absorbent core disposed between said topsheet and said backsheet.

2. The absorbent article of claim 1, wherein said isoflavones are selected from the group consisting of soy isoflavones, clover isoflavones, genestein, daidzein, formononetin, biochanin A, S-equol, R-equol or mixtures thereof.

3. The absorbent article of claim 1, wherein said lotion coating is hydrophobic.

4. The absorbent article according to claim 1, wherein said lower molecular weight glycols or polyols is polypropylene glycol.

5. The absorbent article of claim 4, wherein the molecular weight of the polypropylene glycol is from 425 g/mole to 2025 g/mole.

6. The absorbent article of claim 1, wherein said catamenial device is selected from the group consisting of a sanitary napkin, a pantiliner and an incontinence device.

7. The absorbent article of claim 1, wherein said topsheet is selected from the group consisting of a nonwoven material and a formed film material.

8. The absorbent article of claim 1, wherein said topsheet is hydrophilic.

9. The absorbent article of claim 1, wherein said lotion coating is disposed on said topsheet nonuniformly.

10. The absorbent article of claim 1, wherein said lotion coating is disposed on said topsheet in a stripe generally longitudinally oriented to said article.

11. The absorbent article of claim 1, wherein said topsheet is hydrophobic, said lotion is hydrophobic, and said lotion is disposed on said topsheet in generally parallel stripes.

12. The absorbent article of claim 1, wherein said lotion coating is applied in an amount of from 0.02 mg/cm² to 10.0 mg/cm² of area covered by the lotion.

13. A catamenial device comprising:
   A) a liquid pervious topsheet, said topsheet having an inner surface oriented toward the interior of said absorbent article and an outer surface oriented toward the skin of the wearer when said absorbent article is being worn, wherein at least a portion of said topsheet outer surface comprises an effective amount of a lotion coating which is semi-solid or solid at about 25° C. and which is partially transferable to the wearer's body, said lotion coating comprising:
      (i) from about 60 to about 99.9% of a carrier comprising a petroleum based hydrocarbon,
      (ii) from about 0.2 to about 65% of a fatty alcohol with a melting point from about 45° C. to about 110° C.,
      (iii) from about 0.001 to about 25% of a silk protein, and
      (iv) from 0.001 to 40% of an isoflavone;

B) a backsheet joined to said topsheet; and

C) an absorbent core disposed between said topsheet and said backsheet; and wherein the lotion composition comprises no surfactant.

14. The absorbent article of claim 13, wherein said isoflavones are selected from the group consisting of soy isoflavones, clover isoflavones, genestein, daidzein, formononetin, biochanin A, S-equol, R-equol or mixtures thereof.

15. The absorbent article of claim 13, wherein said lotion coating is hydrophobic.

16. The absorbent article of claim 13, wherein said lotion coating comprises from about 0.025 to about 10% silk protein.

17. The absorbent article of claim 16, wherein said silk protein is selected from the group consisting of silk fiber, sericin, silk amino acids, silk peptides, or mixtures thereof.

18. The absorbent article of claim 13, wherein said catamenial device is selected from the group consisting of a sanitary napkin, a pantiliner and an incontinence device.

19. The absorbent article of claim 13, wherein said topsheet is hydrophobic, said lotion is hydrophobic, and said lotion is disposed on said topsheet in generally parallel stripes.

* * * * *